US010456761B2

(12) United States Patent
Chaussin et al.

(10) Patent No.: US 10,456,761 B2
(45) Date of Patent: Oct. 29, 2019

(54) MIXER-CONTAINER AND METHOD FOR ASSEMBLING A MIXER-CONTAINER INCLUDING A TELESCOPIC SHAFT

(71) Applicant: SARTORIUS STEDIM FMT SAS, Aubagne (FR)

(72) Inventors: Sebastien Chaussin, Aubagne (FR); Jeremy Gibelin, Signes (FR); Stefan Zeuch, Gottingen (DE); Michael Bates, Gloucestershire (GB)

(73) Assignee: SARTORIUS STEDIM FMT SAS, Aubagne (FR)

( * ) Notice: Subject to any disclaimer, the term of this patent is extended or adjusted under 35 U.S.C. 154(b) by 0 days.

(21) Appl. No.: 15/750,048

(22) PCT Filed: Aug. 2, 2016

(86) PCT No.: PCT/FR2016/052017
§ 371 (c)(1),
(2) Date: Feb. 2, 2018

(87) PCT Pub. No.: WO2017/021653
PCT Pub. Date: Feb. 9, 2017

(65) Prior Publication Data
US 2018/0221838 A1 Aug. 9, 2018

(30) Foreign Application Priority Data
Aug. 3, 2015 (FR) .................... 15 57500

(51) Int. Cl.
*B65D 77/06* (2006.01)
*B01F 7/16* (2006.01)
(Continued)

(52) U.S. Cl.
CPC ...... *B01F 13/0836* (2013.01); *B01F 3/04248* (2013.01); *B01F 3/04531* (2013.01);
(Continued)

(58) Field of Classification Search
CPC .... B65D 77/06; B65D 21/086; B65D 90/205; B65D 88/68; B65D 37/00; B65D 88/16;
(Continued)

(56) References Cited

U.S. PATENT DOCUMENTS 7,153,021 B2 * 12/2006 Goodwin ............ B01F 13/0818
366/273
7,278,780 B2 * 10/2007 Goodwin ............ B01F 13/0818
366/273
(Continued)

FOREIGN PATENT DOCUMENTS

DE 2017472 A1 * 11/1971 .......... B01F 13/0827
DE 20 2007 005868 U1 7/2007
(Continued)

OTHER PUBLICATIONS

International Search Report, dated Dec. 16, 2016, from corresponding PCT application No. PCT/FR2016/052017.

*Primary Examiner* — Charles Cooley
(74) *Attorney, Agent, or Firm* — Young & Thompson

(57) ABSTRACT

A method for assembling a mixer-container intended for receiving a biopharmaceutical fluid includes providing a container with a mixing device including at least one shaft having an adjustable length, and at least one first bearing attached to a wall of the container, the shaft extending at least into the inner space from the first bearing; a rigid outer device that compresses the container; and a drive motor located outside the container, the first bearing of the container is placed so as to be spaced apart from the motor, and the length of the shaft is adjusted along the main axis by arranging the shaft opposite the motor to enable the motor to rotate the shaft.

5 Claims, 5 Drawing Sheets

(51) Int. Cl.
    *B01F 15/00* (2006.01)
    *B01F 13/08* (2006.01)
    *B01F 7/00* (2006.01)
    *B01F 7/22* (2006.01)
    *B01F 3/04* (2006.01)
    *C12M 1/00* (2006.01)

(52) U.S. Cl.
    CPC ...... *B01F 7/00633* (2013.01); *B01F 7/00716* (2013.01); *B01F 7/00725* (2013.01); *B01F 7/1695* (2013.01); *B01F 7/22* (2013.01); *B01F 15/0085* (2013.01); *B65D 77/06* (2013.01); *C12M 23/26* (2013.01); *B01F 2003/04326* (2013.01); *B01F 2003/04673* (2013.01); *B01F 2215/0032* (2013.01); *B01F 2215/0073* (2013.01)

(58) Field of Classification Search
    CPC .... B65D 83/0055; A61J 1/05; B01F 15/0085; B01F 7/163; B01F 15/00831; B01F 7/162; B01F 2215/0032; B01F 13/0836; B01F 3/04531; B01F 7/00725; B01F 7/1695; B01F 3/04248; B01F 7/00716; B01F 7/22; B01F 7/00633; B01F 2215/0073; B01F 2003/04326; B01F 2003/04673; C12M 27/02; C12M 23/14; C12M 23/00; C12M 23/26
    USPC ........ 366/273–274, 314, 348, 117, 118, 315, 366/317, 322–335; 435/302.1; 604/416, 604/903; 383/127; 416/3; 206/219–221, 206/818; 215/DIG. 3, DIG. 8
    See application file for complete search history.

(56) References Cited

U.S. PATENT DOCUMENTS

| | | | | |
|---|---|---|---|---|
| 7,832,922 B2 * | 11/2010 | Schoeb | ............... | B01F 7/00716 366/273 |
| 8,845,182 B2 * | 9/2014 | Bernard | .................. | B01F 7/162 366/314 |
| 8,870,443 B2 * | 10/2014 | Greller | ................ | B01F 7/00633 366/102 |
| 8,951,785 B2 * | 2/2015 | Fatherazi | ............ | B01F 7/00058 366/343 |
| 9,044,718 B2 * | 6/2015 | Ludwig | ............... | B01F 3/04269 |
| 9,073,023 B2 * | 7/2015 | Bernard | ................ | B01F 3/1207 |
| 9,266,669 B2 * | 2/2016 | Barbaroux | ............. | B01F 7/163 |
| 9,440,206 B2 * | 9/2016 | Cuting | ................ | B01F 11/0045 |
| 9,840,689 B2 * | 12/2017 | Chaussin | ............... | C12M 29/00 |
| 10,118,141 B2 * | 11/2018 | Larsen | ................ | B01F 7/00691 |
| 10,150,090 B2 * | 12/2018 | Goodwin | ............ | B01F 7/00691 |
| 10,272,400 B2 * | 4/2019 | Staheli | ................ | B01F 7/00058 |
| 2006/0176772 A1 * | 8/2006 | Goodwin | ............ | B01F 13/0818 366/273 |
| 2007/0253287 A1 * | 11/2007 | Myhrberg | ............... | B01F 7/162 366/273 |
| 2009/0142827 A1 * | 6/2009 | Schoeb | ............... | B01F 7/00716 435/302.1 |
| 2010/0260010 A1 * | 10/2010 | Jornitz | .................. | B01F 7/0005 366/343 |
| 2010/0301042 A1 * | 12/2010 | Kahlert | ..................... | B01F 7/18 220/23.86 |
| 2011/0013473 A1 * | 1/2011 | Ludwig | ............... | B01F 3/04269 366/101 |
| 2011/0013474 A1 * | 1/2011 | Ludwig | ............... | B01F 3/04269 366/102 |
| 2011/0026360 A1 * | 2/2011 | Greller | ................ | B01F 7/00633 366/308 |
| 2011/0044567 A1 * | 2/2011 | Barbaroux | ............. | B01F 7/163 383/120 |
| 2011/0158037 A1 * | 6/2011 | Bernard | ................ | B01F 3/1207 366/173.2 |
| 2013/0101982 A1 * | 4/2013 | Goodwin | ............ | B01F 7/00691 435/3 |
| 2014/0366969 A1 * | 12/2014 | Chaussin | ............... | C12M 29/00 137/590 |
| 2014/0369157 A1 * | 12/2014 | Bernard | .................. | B01F 7/162 366/177.1 |
| 2015/0376563 A1 * | 12/2015 | Husemann | ............. | C12M 23/14 435/289.1 |
| 2016/0114951 A1 * | 4/2016 | Barbaroux | ............. | B01F 7/163 220/9.2 |
| 2016/0151749 A1 * | 6/2016 | Seitz | ...................... | F16J 15/002 435/289.1 |
| 2016/0304824 A1 * | 10/2016 | Mahajan | ............... | B01F 7/1695 |
| 2017/0312713 A1 * | 11/2017 | Schob | ................. | B01F 13/0836 |
| 2018/0221838 A1 * | 8/2018 | Chaussin | ............ | B01F 7/00633 |
| 2018/0334645 A1 * | 11/2018 | Schaefer | ............ | C12M 31/10 |
| 2019/0054433 A1 * | 2/2019 | Larsen | ................ | B01F 7/00691 |

FOREIGN PATENT DOCUMENTS

| | | |
|---|---|---|
| DE | 20 2009 005407 U1 | 9/2009 |
| DE | 10 2008 058338 A1 | 5/2010 |
| WO | 2009/143925 A2 | 12/2009 |
| WO | 2014/116165 A1 | 7/2014 |
| WO | 2015/039034 A1 | 3/2015 |

* cited by examiner

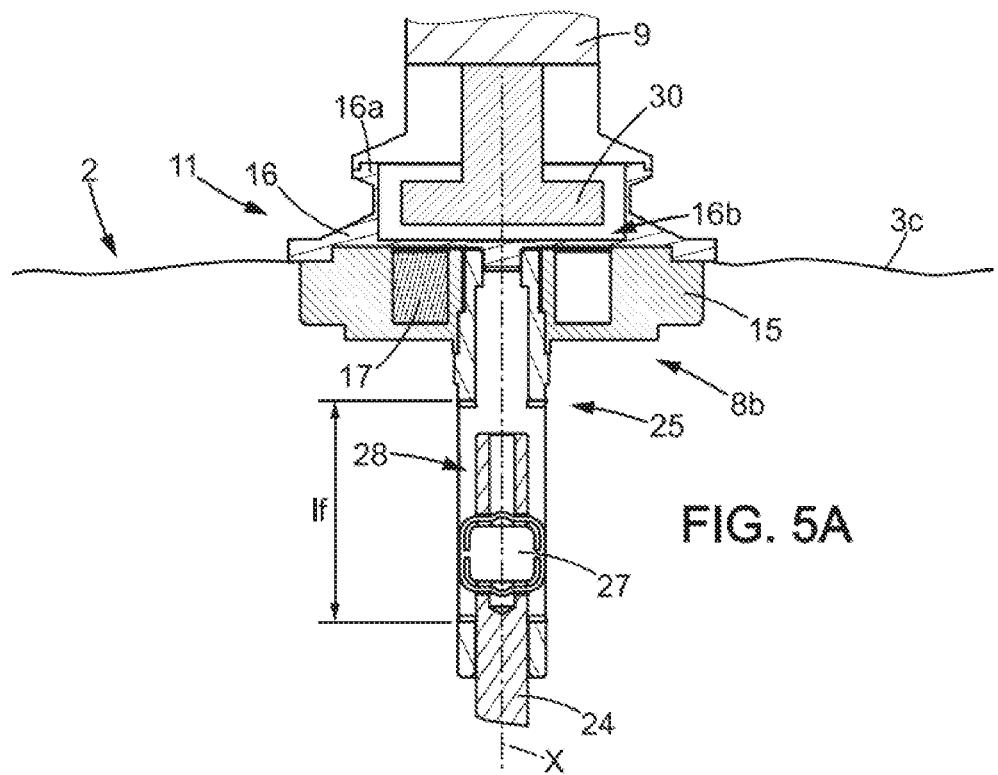
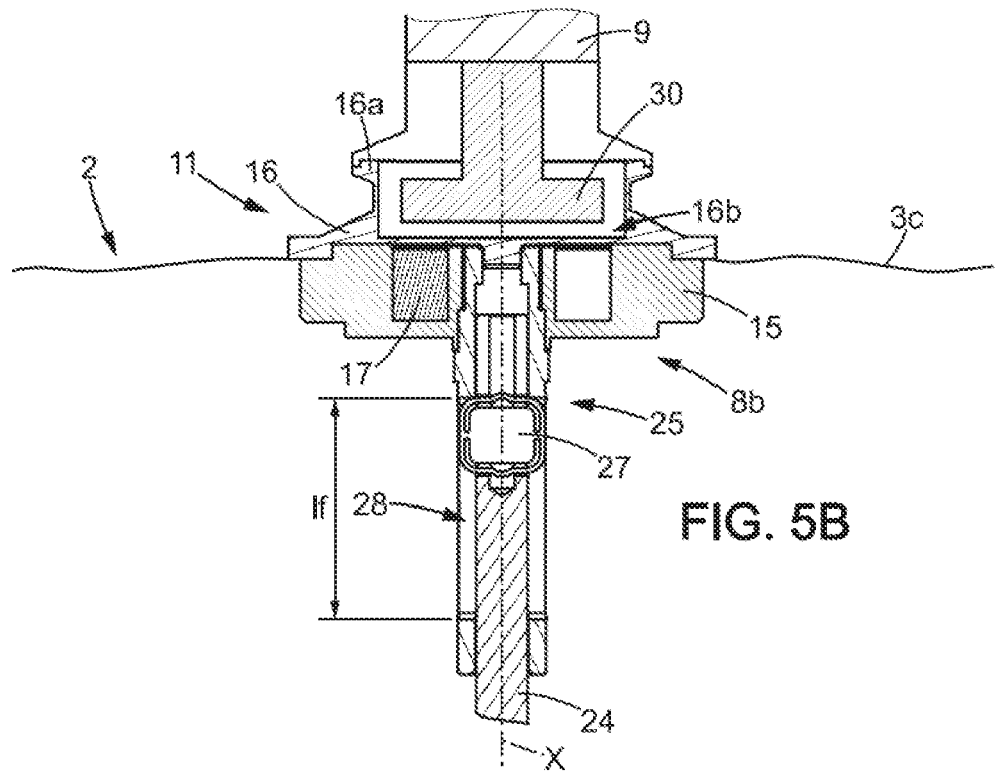

MIXER-CONTAINER AND METHOD FOR ASSEMBLING A MIXER-CONTAINER INCLUDING A TELESCOPIC SHAFT

FIELD OF THE INVENTION

The invention relates to the field of mixer-containers.

It relates more particularly to a method of assembling a mixer-container intended for receiving a biopharmaceutical fluid for mixing, as well as such a mixer-container.

The term "biopharmaceutical fluid" is understood to mean a product of biotechnology (culture media, cell cultures, buffer solutions, artificial nutrition liquids, blood products and blood product derivatives) or a pharmaceutical product or more generally a product intended for use in the medical field. The invention also applies to other products subject to similar requirements regarding packaging.

BACKGROUND OF THE INVENTION

Mixer-containers are known which enable mixing biopharmaceutical fluid. Such mixer-containers comprise an rigid outer containment device forming a housing for receiving a sterile disposable container. The container comprises a flexible wall defining an inner space to be filled with the biopharmaceutical fluid. The container also comprises a mixing member attached to a descending shaft. The shaft is attached to the container at a first bearing and a second bearing. The shaft of the container comprises, at the first bearing, a disc having magnets that can be placed facing a similar disc connected to a motor, the effect of the motor thus magnetically driving the shaft to rotate. The shaft can thus turn in order to mix the biopharmaceutical fluid.

Such a magnetic driving system requires precise alignment and positioning of the magnetic disc of the shaft and the magnetic disc of the motor to ensure optimal driving.

However, problems with geometric tolerances, due to the dimensional variability inherent in the manufacture of the component elements of the mixer-container, can lead to improper positioning of the magnetic discs of the shaft and of the motor facing one another when the container is installed into the rigid outer containment device. Furthermore, when mixing and heating the biopharmaceutical fluid, for example from temperatures of about 30-40 degrees Celsius, dilation of the plastic parts forming the mixer-container may occur. This changes the arrangement and position of the first bearing of the shaft relative to the motor, leading to improper operation of the mixer-container. It is then necessary to be able to adjust the positioning of the first bearing relative to the motor.

It is thus known to use a motor whose position is adjustable in height. However, the adjustment of such a motor can be difficult. If the motor is positioned too low, the arrangement of the first bearing and motor exerts stress on the shaft, which may result in bending or even breaking the shaft. In addition, an axial runout clearance of about 2 millimeters is required between the first bearing and the motor of the magnetic disc to allow the mixer-container to operate satisfactorily. A motor attached too low does not permit this clearance to exist, generating abrasion at the first bearing during operation of the mixer-container.

Conversely, if the motor is positioned too high, the container wall is subjected to tensile stress so that the motor and the first bearing can be positioned by each other. These stresses can damage the container wall, or even cause a tear resulting in a loss of biopharmaceutical fluid.

Adjustment and positioning of the motor can therefore be long and complicated in order to obtain satisfactory installation of the container in the rigid containment device.

Also known are containers comprising variable-length shafts, which enable folding the container by shortening the length of the shaft and facilitate container storage.

For example, patent WO 2015/039034 discloses bioreactor support structures comprising a telescopic shaft that can be used with containers of various sizes and shapes.

U.S. Pat. No. 8,951,785 discloses a stirrer for a bioreactor, having a plurality of hingedly interconnected arms pivotable about a transverse axis of rotation. The shaft can thus have an adjustable height by folding the hinged arms.

WO 2009/143925 discloses a container having two adjacent shaft members each having a hollow body into which one of the two shaft members can slide. An elastic member is located between the hollow body and the filling body in order to allow transmission of rotational movement between the two members. An opening is provided in the wall of the hollow body, to balance the pressure in the hollow body and in the rest of the container. A hydrophobic gas-permeable membrane is placed across the opening to prevent fluid entering the hollow body from the container.

However, such a shaft is difficult to implement since it is necessary to provide a hydrophobic membrane over the opening of the hollow body. Furthermore, in the case of a circular shaft, the elastic member only allows transmitting low torques, preventing efficient mixing of the fluid filling the container.

OBJECTS AND SUMMARY OF THE INVENTION

The invention aims to solve the disadvantages described above, and in particular aims to optimize the introduction of the container into the rigid outer containment device in order to provide satisfactory mixing of the biopharmaceutical fluid.

For this purpose, in a first aspect, the invention relates to a method for assembling a mixer-container intended for receiving a biopharmaceutical fluid for mixing, wherein:
  a container is provided having a flexible wall defining an inner space suitable for filling with biopharmaceutical fluid, the container comprising:
    a mixing device comprising at least one shaft having an adjustable length along a main axis,
    at least one first bearing attached to the wall, the shaft extending at least into the inner space from the first bearing,
  a rigid outer containment device for the container is provided,
  a drive motor located outside the container is provided, the motor being suitable for rotating the shaft of the mixing device,
  the container is placed in the rigid outer containment device, the rigid outer containment device comprising a bottom wall and a peripheral wall defining a housing adapted to receive the container, the flexible wall of the container being arranged on the bottom wall of the rigid outer containment device, and
  the length of the shaft along the main axis is adjusted while arranging the shaft facing the motor to enable the motor to rotate the shaft.

In various embodiments of the present invention, one or more of the following arrangements may possibly further be employed, separately or in combination:

the container is in a disassembled state empty of biopharmaceutical fluid when placed in the rigid outer containment device;

the length of the shaft is adjustable up to a length corresponding substantially to the axial dimension of the motor;

the shaft is located entirely within the inner space and the length of the shaft along the main axis is adjusted while positioning the first bearing facing the motor to enable the motor to rotate the shaft; and the container also comprises a second bearing attached to the wall, and the second bearing is connected to the rigid outer containment device after the container is placed in the rigid outer containment device.

According to a second aspect, the invention relates to a mixer-container intended to be assembled by the assembly method according to the invention, comprising:

a container having a flexible wall defining an inner space suitable for filling with biopharmaceutical fluid, the container comprising:

a mixing device comprising at least one shaft having an adjustable length along a main axis, at least one first bearing, the shaft extending at least into the inner space from the first bearing, a drive motor located outside the container, the motor being suitable for rotating the shaft of the mixing device, and a rigid outer containment device comprising a bottom wall and a peripheral wall defining a housing adapted to receive the container.

In various embodiments of the present invention, one or more of the following arrangements may possibly be employed, separately or in combination:

the motor is fixed relative to the rigid outer containment device;

the motor is adapted to enable magnetically driving the shaft and comprises a rotary driving disc located outside the container, the rotary driving disc operatively engaging with a rotary driven disc attached to the shaft;

the first bearing comprises a flange, the flange comprising an outer annular collar, the motor being connected with the collar of the flange; and a bioreaction is carried out, the mixer-container being a bioreactor.

According to a third aspect, the invention relates to a container intended to be assembled to a motor according to the assembly method, in order to form a mixer-container according to the invention.

In various embodiments of the present invention, one or more of the following arrangements may possibly be employed, separately or in combination:

the shaft is located entirely within the inner space;

the shaft traverses the first bearing;

the shaft supports and drives at least one mixing member adapted to mix the biopharmaceutical fluid located in the inner space;

the shaft supports and drives multiple mixing members located at a plurality of axial locations on the shaft;

the container has a capacity of between 50 liters and 200 liters; and the container is disposable.

According to a fourth aspect, the invention relates to a mixing device comprising a shaft of adjustable length extending between a first bearing and a second bearing, each among the first bearing and second bearing being attached to the flexible wall of a container according to the invention.

In various embodiments of the present invention, one or more of the following arrangements may possibly be employed, separately or in combination:

the shaft comprises at least a first part and a second part which are movable in translation relative to one another along the main axis;

the first part comprises a member adapted to slide in a rectilinear slot of the second part of the shaft;

the slot traverses the second part of the shaft from one side to the other;

the slot has a length between 1 and 10 centimeters, preferably equal to 5 centimeters; and the first part and the second part of the shaft are integral in rotation.

BRIEF DESCRIPTION OF THE DRAWINGS

We will now describe several embodiments of the invention with the aid of the drawings, in which:

FIGS. 5A and 5B are enlarged views of the shaft of the mixing device at the first bearing of FIG. 4 in two different arrangements.

MORE DETAILED DESCRIPTION

A mixer-container 1 according to the invention is adapted to receive a biopharmaceutical fluid C for mixing, or where appropriate for a chemical and/or biological reaction (or bioreaction), the mixer-container 1 then being a bioreactor.

The biopharmaceutical fluid C comprises one or at least one liquid phase. Where appropriate, the biopharmaceutical fluid C is formed from multiple components of which at least one is in a liquid phase and of which one or more may be in a solid phase, such as powder.

The mixer-container 1 has a vertical main axis XX. The mixer-container 1 comprises a container 2 and a rigid outer containment device 18.

Figure 3:
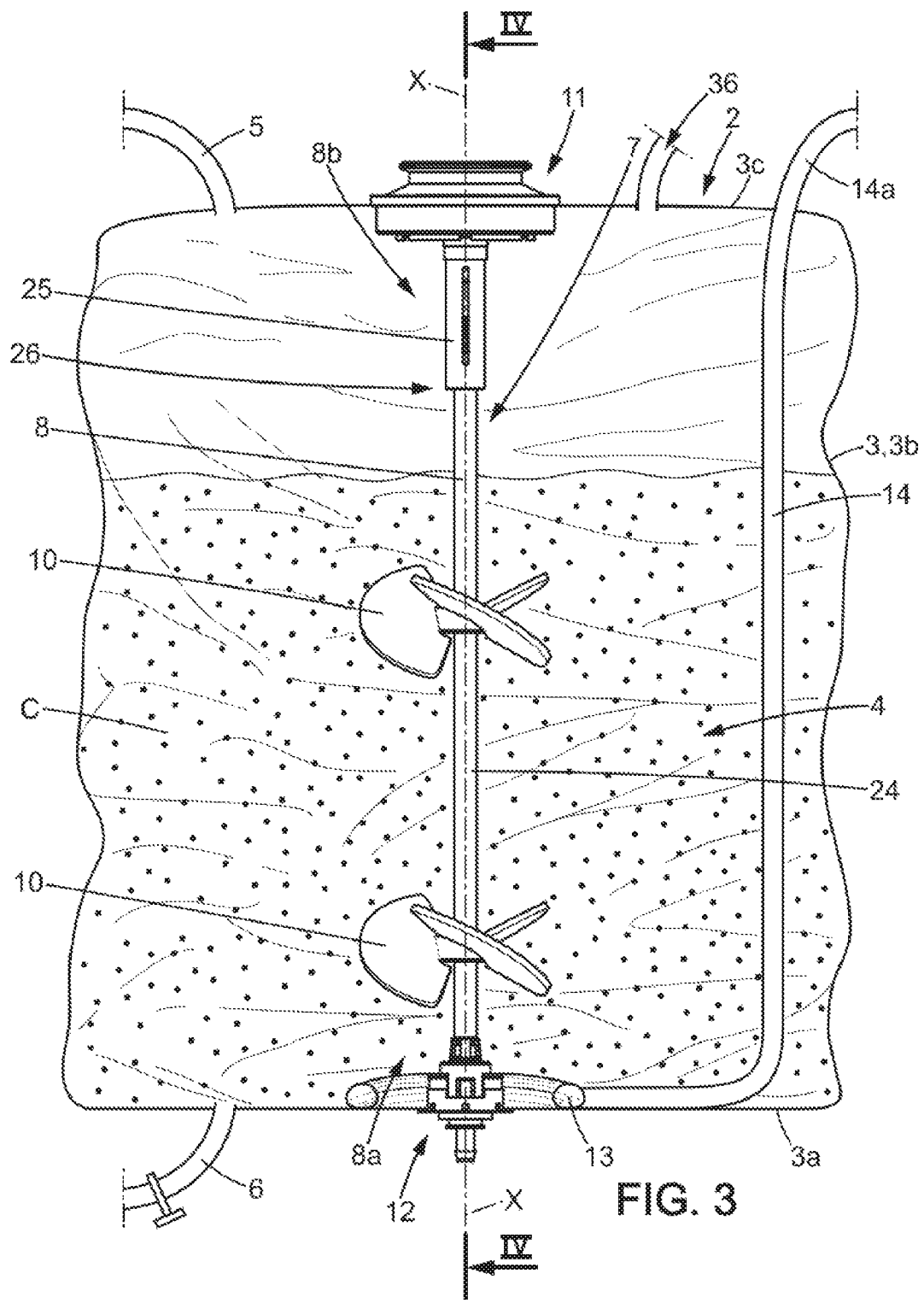
FIG. 3 is a side view of a container intended to be placed in the rigid outer containment device of FIGS. 1 and 2.

As represented in FIG. 3, the container 2 is formed by a wall 3, advantageously made of plastic, flexible and fluidtight to the biopharmaceutical fluid C. The wall 3 of the container 2 may comprise a bottom part 3a, a side part 3b, and an upper part 3c, for example formed by one or more welded sections made integral to one another. The container 2 thus defines an inner space 4, advantageously sterile, suitable for receiving a quantity of biopharmaceutical fluid C. The wall 3 may be completely or partially transparent or translucent in order to be able to view the biopharmaceutical fluid C within the inner space 4, from the exterior.

According to one embodiment, the container 2 is disposable.

The container 2 may have a capacity of up to 5000 liters, depending on requirements and applications. However, the container 2 preferably has a capacity of between 10 and 500 liters, more preferably between 50 and 200 liters.

The words "vertical", "horizontal", "upper", "lower", refer to the situation in which the mixer-container 1, and particularly the container 2, is in a position suitable for operation. It is understood, however, that the mixer-container 1 and the container 2 may occupy other positions or be in other states, for example when they are not in operation. The word "vertical" should not be understood in a narrow sense, but in sense meaning from highest to lowest and vice versa.

The words "inner", and "outer" or "exterior" or "outside", respectively refer to within the inner space 4 and outside of the container 2.

Finally, the word "axial" on the one hand, and the words "radial" and "transverse" on the other hand, refer to what extends in or parallel or substantially parallel to the main axis XX for the former, and perpendicularly or orthogonally or substantially perpendicularly or orthogonally to the main axis XX for the latter.

The mixer-container 1 may comprise one or more through-ports 5 for introducing into the container 2 the biopharmaceutical fluid C, or components of the biopharmaceutical fluid C; these ports engage with one or more fill holes formed in the container 2.

The mixer-container 1 may also comprise at least one through-port 6 for draining biopharmaceutical fluid C from the container 2, engaging with at least one drain hole formed in the container 2. The drain port 6 is able to be closed when necessary and opened for draining.

The term "port" is understood to refer to a physical connection means. Such a port is a through-port when it places in communication the inner space 4 and the exterior of the container 2, for example for the introduction or discharge of what is to be placed or has been placed in the container 2. Such a port may also not be a non-through-port when it serves to hold a member of the mixer-container.

Ducts, pouches, reservoirs, if necessary flexible, may be associated with the introduction port 5, in fluid communication and with a sealed connection and removable where appropriate. Similarly, ducts, pouches, reservoirs, if necessary flexible, may be associated with the drain port 6, in fluid communication and with a sealed connection and removable where appropriate.

Figure 4:
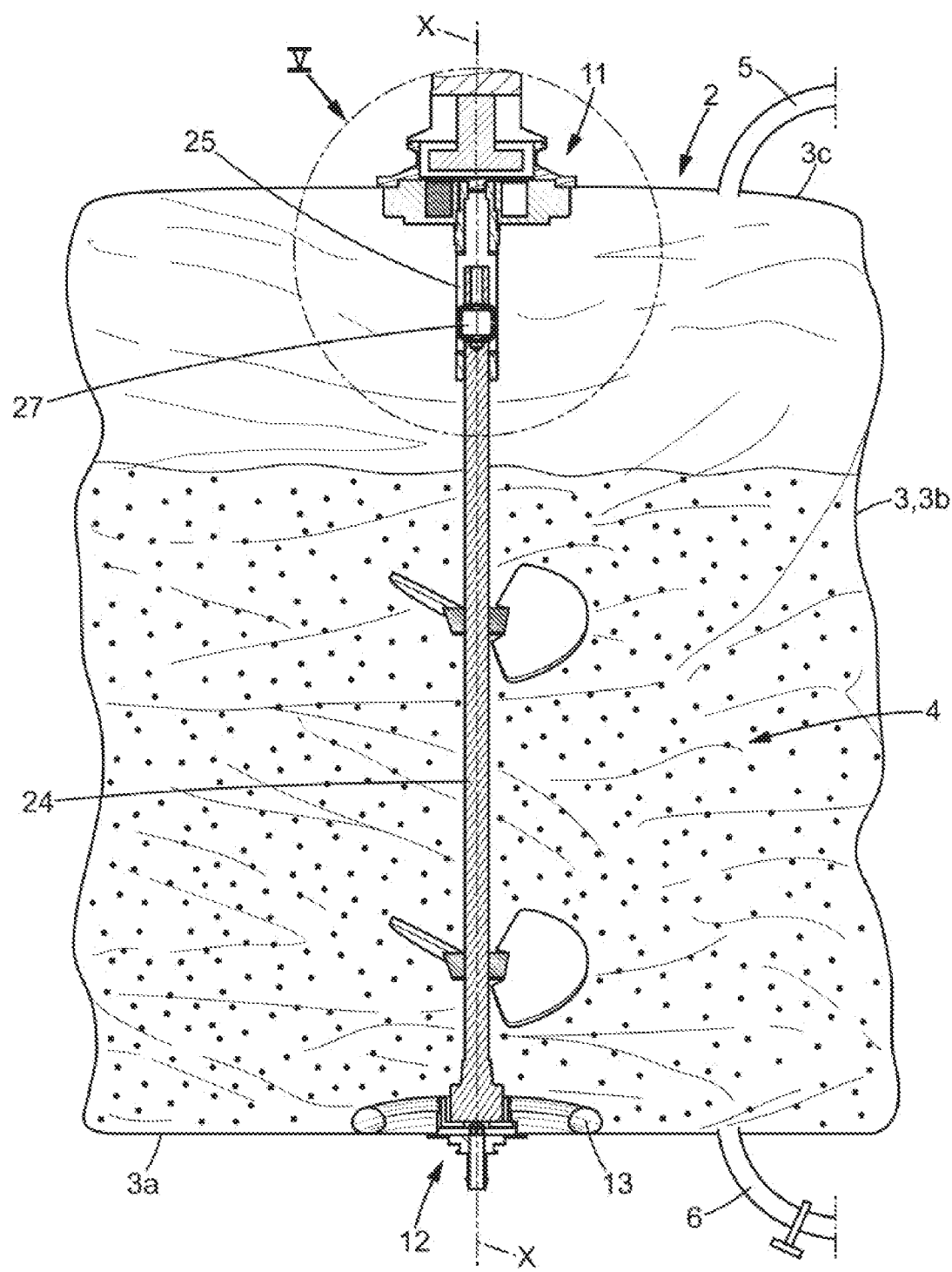
FIG. 4 is a sectional view along plane IV-IV of the container of FIG. 3, positioned relative to a motor.

In the embodiment represented in FIGS. 3 and 4, the introduction port 5 is located in the upper part 3c of the wall 3, while the drain port 6 is located in the lower part 3a of the container 2, in particular in the lowest position of the mixer-container 1. However, this embodiment is not limiting and one or more introduction ports 5 may be located in the lower part 3a or in the side part 3b of the container 2.

The mixer-container 1 may also comprise an aeration device 13 adapted to deliver to the biopharmaceutical fluid C a certain quantity of aeration gas. This device 13 thus allows aeration of what is in the inner space 4 of the container 2, whether it is biopharmaceutical fluid or part of its components.

The aeration device 13 may comprise an aeration gas supply device 14 having at least one tubular element 14a extending from outside the container 2 with fluid communication. There may be operatively associated, with the aeration device 13 just described, at least one aeration gas discharge port 36 formed in the upper part 3c of the wall 3 of the container 2. Such an aeration gas discharge port 36 serves to discharge from the container 2, to the exterior, gas that has not been mixed with the biopharmaceutical fluid C of the container 2.

In some embodiments, the mixer-container 1 may also comprise other ports which are known per se, for example for mounting an operative means, suitable for retaining a member typically for the collection or measurement of data for example, or sample collection for analysis.

The mixer-container 1 also comprises a device 7 for mixing the biopharmaceutical fluid C of the container 2. This mixing device 7 allows mixing what is in the inner space 4 of the container 2, whether this is biopharmaceutical fluid C or some of its components.

Figure 6:
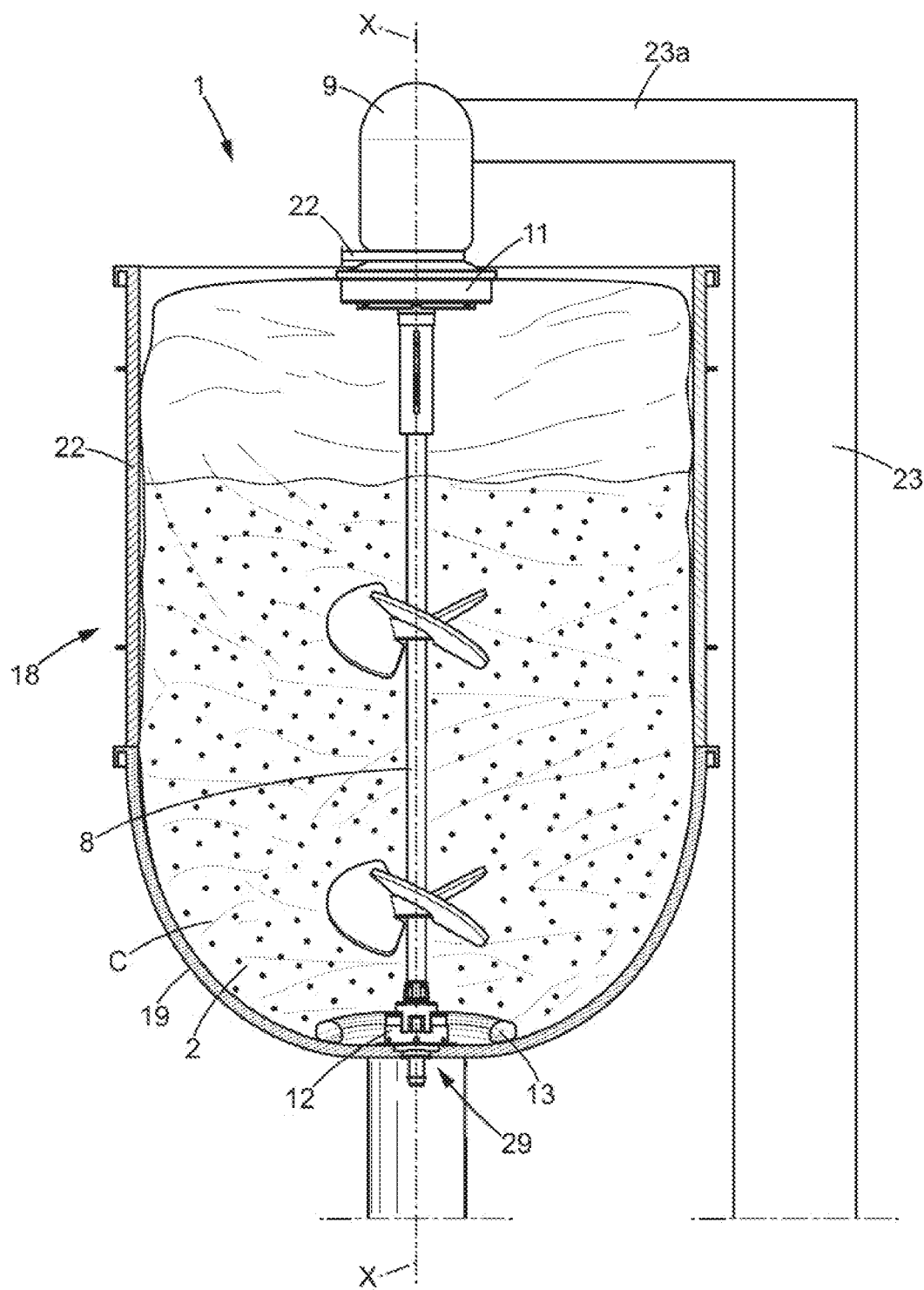
FIG. 6 is a schematic sectional view of the container placed in the rigid outer containment device of the mixer-container in the operating state, in particular in a filled assembled state.

The mixing device 7 comprises at least one descending shaft 8, adapted to be rotated, in particular magnetically, by a motor 9 and to rotate at least one mixing member 10. The mixing member or members 10 are substantially distanced from the lower part 3a and the side part 3b of the wall 3 of the container 2. As represented in FIGS. 3, 4, and 6, the mixing member 10 may be in the form of a propeller having a hub carrying several blades.

The shaft 8 according to the invention is adjustable in length. According to the embodiment represented in the figures, the shaft 8 is thus formed of two parts 24, 25. A first part 24 extends from the lower end 8a to an intermediate connection area 26, while the second part 25 extends from the connection area 26 to the upper end 8b.

As represented in more detail in FIGS. 5A and 5B, the first part 24 of the shaft 8 at the connection area 26 comprises a member 27, such as a cotter, housed in a slot 28 of the second part 25 of the shaft 8. The slot 28 extends rectilinearly along the main axis XX. The slot 28 entirely traverses the second part 25 of the shaft 8. The member 27 then has a non-flat shape, in particular square, in order to enter the slot 28 traversing the second part 25 of the shaft 8.

The first part 24, in particular the member 27, is adapted to slide in the second part 25 of the shaft 8 along the main axis XX. As represented in FIGS. 5A and 5B, the slot 28 has a length $I_f$, for example between 1 and 10 cm, preferably equal to about 5 centimeters. In particular, the length $I_f$ can be adjusted according to the size of the container 2. Thus, the shaft 8 is adjustable in length between a fully extended position and a fully retracted position. In the fully retracted position as represented in FIG. 5B, the shaft 8 has a minimal height, the first part 24, in particular member 27, coming into abutment with the second part 25 of the shaft 8.

The member 27 is adapted to slide continuously in the slot 28. The shaft 8 can therefore have a continuously adjustable length, not discrete, for example in case of expansion of some members of the mixer-container 1 during mixing.

In addition, due to the fact that the member 27 projects into the slot 28, the first part 24 and second part 25 of the shaft 8 are integral in rotation, in particular when subjected to high torques.

In addition, since the shaft 8 has an adjustable length, the motor 9 can be fixed relative to the outer containment device 18, and it is not necessary for it to have an adjustable position, in particular in height, in order to place the shaft 8 facing the motor 9 to allow rotation of the shaft 8 as will be described below.

The container 2 also comprises at least a first bearing 11, adjacent to the upper part 3c of the wall 3, which engages with the upper part 8b of the shaft 8.

The first bearing 11 comprises a rigid flange 16. "Flange" is understood here to mean a rigid piece having the general form of a solid wall, at least substantially flat, laid flat and intended for retention. This flange 16 is rigidly and sealingly fixed to the upper part 3c of the wall 3 of the container 2.

More specifically, the flange 16 is formed of a substantially rigid material, preferably a rigid plastic material, in the shape of a wall or plate connected to the container 2 at the center of the upper part 3c. This flange 16 may be connected to the wall 3 of the container 2 in any suitable manner so as to form a rigid and hermetic seal between the respective rigid and flexible materials of the flange 16 and the wall 3.

According to a first embodiment, the shaft 8 of the mixing device 7 is located entirely within the inner space 4. The shaft 8 thus extends rectilinearly between a lower end 8a and an upper end 8b. When the mixer-container 1 is in a position suitable for operation, the shaft 8 extends vertically along the main axis XX, the lower end 8a being located towards the lower part 3a of the container 2 while the upper end 8b is located towards the upper part 3c of the container 2, in particular connected to the first bearing 11. The first bearing 11 is then adapted to be positioned relative to the motor 9 located outside the container 2.

According to the first embodiment represented for example in FIGS. 5A and 5B, the drive motor 9 magnetically drives the shaft 8 to rotate. For this purpose, the motor 9 comprises a rotary driving disc 30 located outside the container 2. The shaft 8 then comprises a rotary driven disc 15 for operatively engaging, in particular magnetically, with the rotary driving disc 30 of the motor 9. More particularly, the rotary driven disc 15 comprises a plurality of magnets 17, which are integrated by any means of attachment or construction, in order to enable rotation of the shaft 8 during rotation of the rotary driving disc of the motor 9.

The rotary driven disc 15 is integral, in particular in rotation, with the shaft 8, in particular with the second part 25 of the shaft 8. For example, the rotary driven disc 15 is fixed to the upper end 8b of the shaft 8 by screwing a threaded end of the shaft 8 into a threaded opening within the rotary driven disc 15. Other means, such as adhesives, fasteners, quick fasteners, bolts, welding, and the like, as well as formation of the rotary driven disc 15 directly by molding with the shaft 8 during its manufacture, may be used to fix the rotary driven disc 15 to the shaft 8, without limitation.

In addition, the rotary driven disc 15 is connected to the first bearing 11, in particular to the flange 16, so as to allow the motor 9 to act on the magnets 17 of the rotary driven disc 15. Thus, the flange 16 is connected to the shaft 8 within the inner space 4 of the container 2 via the rotary driven disc 15. In particular, the shaft 8 and the rotary driven disc 15 are mounted so as to rotate about the main axis XX relative to the first bearing 11, so that the rotary driven disc 15 can rotate relatively freely with respect to the flange 16. To this end, provision may be made to include ball bearings or roller bearings between the rotary driven disc 15 and the first bearing 11.

When in the operating state, the first bearing 11 is positioned, in particular assembled, relative to the motor 9. The rotary driving disc 30 of the motor 9 and the rotary driven disc 15 are then arranged facing one another, on each side of the first bearing 11. There may be provided a runout clearance between the rotary driving disc 30 and the first bearing 11, for example of about 2 millimeters, to facilitate rotation of the first bearing 11 relative to the motor 9.

The first bearing 11, in particular the flange 16, comprises for example an outer annular collar 16a comprising a terminal radial bead extending laterally outwardly and inwardly delimiting a cavity 16b of the flange 16. The motor 9 can be positioned relative to the flange 16 and in particular with the collar 16a fixed in translation. In particular, the rotary driving disc 30 of the motor 9 is to be arranged within the cavity 16b of the flange 16 as represented in FIGS. 5A and 5B.

As represented in FIG. 6, a clamp 22 connects the flange 16 with the motor 9. Such a clamp conventionally comprises a clamping cuff and is known as a "tri-clamp". The clamp 22 is adapted and intended to clamp on to the motor 9 and collar 16a of the flange 16, keeping them integral in translation to prevent their accidental disassembly. However, the motor 9 remains rotatable relative to the first bearing 11 about the main axis XX. Thus, the rotary driving disc 30 of the motor 9 can rotate the rotary driven disc 15.

According to a second embodiment not represented in the figures, the shaft 8 may be partially located outside of the container 2. According to this embodiment, the shaft 8 passes through the container 2, in particular at the first bearing 11 in a fluidtight manner. The rotary driven disc 15 of the shaft is then located outside the container 2 and is designed to engage functionally, in particular magnetically, with the rotary driving disc 30 of the motor 9.

According to this embodiment, the connection area 26 of the shaft 8 can be located outside the container 2. The length of the shaft 8 can be easily adjusted from outside the container 2 by the user of the mixer-container 1, which allows obtaining a container 2 that is simple to use and economical to produce. In addition, the connection area 26 is then easier to access, which facilitates its sterilization prior to use of the container 2.

The mixer-container 1 may also comprise, due to the flexible nature of the container 2, a rigid, possibly semi-rigid, outer containment device 18 for the container 2 filled with biopharmaceutical fluid C, for use during filling, mixing, and draining.

The rigid outer containment device 18 comprises a bottom wall 19 and a peripheral wall 20 defining a housing into which the container 2 is removably placed. For example, the bottom wall 19 has the shape of a rounded cap, for example hemispherical or pseudo-hemispherical. However, the rigid outer containment device 18 may have any other shape, such as cylindrical, parallelepipedic, or other shapes.

The lower part 3a of the wall 3 of the container 2 rests on the bottom wall 19, while the side part 3b of the wall 3 of the container 2 presses against the peripheral wall 20 when the container 2 is filled with biopharmaceutical fluid C. The rigid outer containment device 18 is generally of identical geometry, shape, and/or dimension to the container 2, in order to reduce the mechanical stresses or forces on the wall 3 of the container 2.

The rigid outer containment device 18 may comprise an access opening 21 to allow the introduction and removal of the container 2. If desired, the rigid outer containment device 18 comprises a closure means, such as doors, in order to permit alternately opening or closing the access opening 21.

In one embodiment, the rigid outer containment device 18 comprises other openings for introducing the biopharmaceutical fluid C or components of the biopharmaceutical fluid C and for draining the biopharmaceutical fluid C, or for accessing the different members of the container 2 which must be accessible for use.

Figure 1:
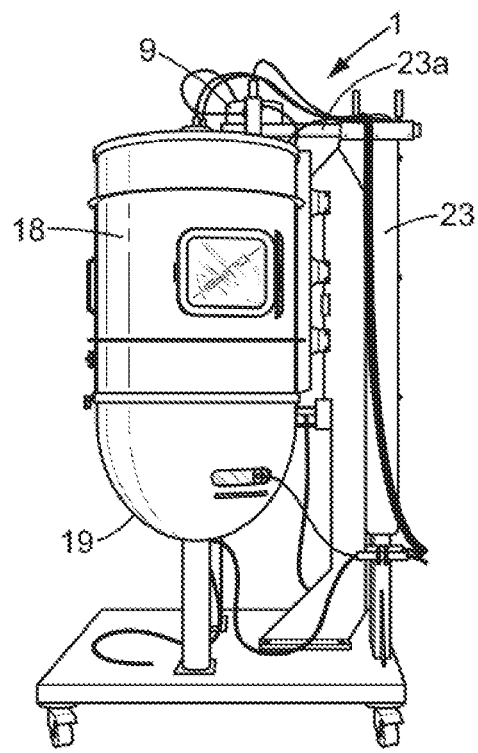
FIG. 1 is a perspective view of one possible embodiment of a mixer-container according to the invention, showing the rigid outer containment device.
Figure 2:
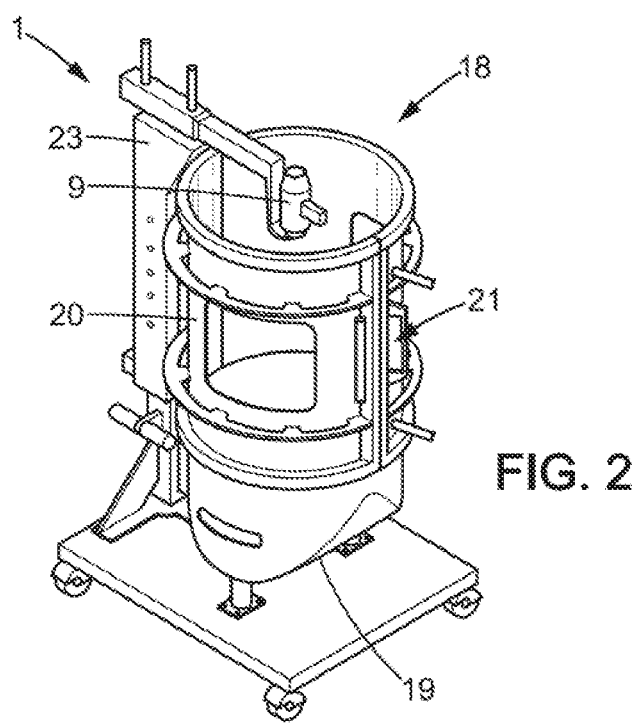
FIG. 2 is another perspective view of the rigid outer containment device of the mixer-container of FIG. 1.

The motor 9 is advantageously placed fixedly above the rigid outer containment device 18. As is represented more particularly in FIGS. 1 and 2, the motor 9 may in particular be fixed to a supporting arm 23 having a transverse portion 23a. Due to this transverse portion 23a of the supporting arm 23, the motor 9 is more particularly centered over the rigid outer containment device 18, along the main axis XX.

In one embodiment, the rigid outer containment device 18 also comprises a heating and/or cooling device for heating and/or cooling the biopharmaceutical fluid C of the container 2. In this case, the rigid outer containment device 18 and/or the container 2 are made of a material having a certain thermal conductivity, so that use of the heating and/or cooling device enables heating and/or cooling the biopharmaceutical fluid C. In this case, and where appropriate, there is also provided a device for controlling the temperature of the content in the container 2 and a device for controlling the heating and/or cooling device. Such a temperature control device can be supported by one or more ports provided for this purpose.

The container 2 may comprise a single first bearing 11 to be positioned relative to the motor 9. However, alternatively, the container 2 may further comprise a second bearing 12 adjacent to the lower part 3*a* of the wall 3, which engages with the lower part 8*a* of the shaft 8. In the same manner as the first bearing 11, the second bearing 12 is connected to the wall 3 of the container 2 to form a rigid and fluidtight seal with the bottom part 3*a* of the wall 3. For this purpose, the second bearing 12 comprises a flange (this term is to be understood as above) fixed in a rigid and fluidtight manner to the lower part 3*a* of the wall 3 of the container 2.

The container 2 is then connected at the second bearing 12 to the outer containment device 18. According to the first embodiment described above wherein the shaft 8 of the mixing device 7 is located entirely within the inner space 4, it is thus possible to adjust the size of the container 2 by adjusting the length of the shaft 8 which extends between the first bearing 11 and the second bearing 12.

The container 2 can be in three different states relative to the rigid outer containment device 18:
- an empty disassembled state, wherein the container 2 is disassembled from the rigid outer containment device 18 and is not positioned relative to the motor 9. In this state, the container 2, which is flexible overall when it is empty of biopharmaceutical fluid C, can be flattened on itself. This state is particularly useful for storage or transport;
- an empty assembled state, wherein the container 2 is connected to the rigid outer containment device 18, the container 2 being empty of biopharmaceutical fluid C. In this state, the container 2 is arranged in the housing of the containment device 18 by resting on the bottom wall 19. "Assembly" is understood to mean the fact that the container 2 operatively interacts with the motor 9. However, such an assembly is not limited to direct contact between the container 2 and the motor 9; these elements can be assembled according to the invention while being spaced apart from one another, for example in a magnetically driven context; and
- finally, a partially assembled or completely filled state, wherein the container 2 is assembled to the rigid outer containment device 18 and positioned relative to the motor 9, the container 2 being filled with biopharmaceutical fluid C. In this state, the mixer-container 1 is functional, suitable for mixing the biopharmaceutical fluid C.

The following describes the method for assembling a mixer-container 1 according to the first embodiment, in particular in order to change between the different states of the container 2 described above.

We begin with a mixer-container 1, the container 2 being in a state of disassembly from the rigid outer containment device 18, as well as empty of biopharmaceutical fluid C and more or less flattened on itself.

The container 2 is placed in the housing within the rigid outer containment device 18, resting on its bottom wall 19.

The second bearing 12 of the container 2 is connected to the rigid outer containment device 18, for example with an opening 29 located at the center of the bottom wall 19.

Then the first bearing 11 of the container 2 is positioned with respect to the motor 9. The wall 3 of the container 2 is therefore brought to the level of the motor 9.

The shaft 8 is then in an at least partially retracted position. Because the shaft 8 is adjustable in length, it is possible to first place the upper end 8*b*, particularly the first bearing 11, at a distance away from the motor 9. The first bearing 11 may in particular be placed in the immediate vicinity of the motor 9, for example at a distance from the motor 9 of less than the length $l_f$ of the slot 28. The rotary driven disc 15 is then located facing the motor 9. Next, the length of the shaft 8 is increased so that the first bearing 11 is positioned next to the motor 9, in particular connected without friction and with a runout clearance between the rotary driving disc 30 of the motor 9 and the first bearing 11, so that the motor 9 can rotate easily.

In order to adjust the length of the shaft 8, the relative sliding of the two parts 24, 25 of the shaft 8 can be done manually or with any other tool enabling such sliding. It is thus not necessary to vary the position of the motor when connecting the first bearing 11 with the motor 9. The container 2 is thus assembled with the rigid outer containment device 18 more easily and optimally.

The motor 9 is connected with the collar 16*a* of the flange 16 so as to be integral in translation, via the clamp 22 (tri-clamp cuff). Thus arranged, the rotary driving disc 9 of the motor 9 is able to rotate the rotary driven disc 15, and thus the shaft 8 of the mixing device 7. FIG. 6 shows the container 2 thus arranged with the rigid outer containment device 18 and the motor 9.

Alternatively, it is possible to connect the first bearing 11 of the container 2 with the motor 9 before connecting the second bearing 12 with the rigid outer containment device 18.

The biopharmaceutical fluid C is introduced into the container 2, by means of the introduction port 5.

Finally, the mixing device 7 is used to stir the biopharmaceutical fluid C of the container 2 located in the inner space 4. If required, the length of the shaft adjusts to guarantee the optimal relative positioning of the motor 9 and the first bearing 11.

In the context of a bioreaction process, the aeration device 13 is used to deliver a certain amount of aeration gas into the contents of the container 2 located in the inner space 4. Stirring and aeration are carried out at least partially simultaneously, where appropriate entirely simultaneously.

After mixing the biopharmaceutical fluid C and then draining it, in particular through the drain port 6, the container 2 is disassembled from the rigid outer containment device 18. The container 2 is then discarded, as it is disposable.

The method described above may be carried out only partially, as the steps described above can be carried out independently of one another. In particular, the container 2 can be arranged in the rigid outer containment device 18 when it is already filled with biopharmaceutical fluid C.

Obviously, the invention is not limited to the embodiments described above and provided only as examples. It encompasses various modifications, alternative forms, and other variants conceivable to a person skilled in the art in the context of the invention, in particular any combination of the different modes of operation described above, which may be taken separately or in combination.

The invention claimed is:

1. A method for assembling a mixer-container intended for receiving a biopharmaceutical fluid for mixing, wherein:

a container is provided having a flexible wall defining an inner space suitable for filling with biopharmaceutical fluid, the container comprising:
- a mixing device comprising at least one shaft having an adjustable length along a main axis, and
- at least one first bearing attached to the wall, the shaft extending at least into the inner space from the first bearing, a rigid outer containment device for the container is provided, a drive motor located outside the container is provided, the motor being suitable for rotating the shaft of the mixing device, the container is placed in the rigid outer containment device, the rigid outer containment device comprising a bottom wall and a peripheral wall defining a housing adapted to receive the container, the flexible wall of the container being arranged on the bottom wall of the rigid outer containment device, and the length of the shaft along the main axis is adjusted to position the shaft facing the motor to enable the motor to rotate the shaft.

2. The method according to the claim 1, wherein the container is in a disassembled state empty of biopharmaceutical fluid when placed in the rigid outer containment device.

3. The method according to claim 1, wherein the length of the shaft is adjustable up to a length corresponding substantially to the axial dimension of the motor.

4. The method according to claim 1, wherein the shaft is located entirely within the inner space and the length of the shaft along the main axis is adjusted while positioning the first bearing facing the motor to enable the motor to rotate the shaft.

5. The method according to claim 1, wherein the container also comprises a second bearing fixed to the wall and the second bearing is connected to the rigid outer containment device after placing the container in the rigid outer containment device.

* * * * *